United States Patent [19]

Stoner et al.

[11] Patent Number: 5,665,340

[45] Date of Patent: Sep. 9, 1997

[54] COMBINED TWO-PART REDUCING AGENT/ HUMECTANT SHAVING SYSTEM FOR IMPROVED SHAVING COMFORT

[75] Inventors: Karla Leum Stoner, Frederick; Charles W. Slife, New Market, both of Md.

[73] Assignee: The Gillette Company, Boston, Mass.

[21] Appl. No.: 584,765

[22] Filed: Jan. 11, 1996

Related U.S. Application Data

[62] Division of Ser. No. 247,915, May 23, 1994, Pat. No. 5,500,210.

[51] Int. Cl.⁶ .................................................. A61K 7/15
[52] U.S. Cl. .................... 424/73; 424/70.5; 424/70.51; 424/70.4
[58] Field of Search ................. 424/70.5, 73, 70.51, 424/70.4

[56] References Cited

U.S. PATENT DOCUMENTS

| | | | |
|---|---|---|---|
| 4,982,750 | 1/1991 | Kaitz | 424/70.5 |
| 5,500,210 | 3/1996 | Stoner | 424/73 |

*Primary Examiner*—Thurman K. Page
*Assistant Examiner*—James M. Spear
*Attorney, Agent, or Firm*—Stephan P. Williams

[57] ABSTRACT

The present invention relates to a method of improving shaving comfort by softening the hair to be shaved so as to reduce the cutting force required to cut it. The novel method comprises carrying out the following sequential steps:

(a) contacting an area of hair to be shaved with a reducing agent that breaks disulfide linkages in hair;

(b) contacting the area of hair treated in step (a) with a humectant and allowing it to dry or partially dry;

(c) contacting the area treated in step (b) with water to hydrate the hair; and (d) shaving the hydrated hair of step (c).

5 Claims, No Drawings

COMBINED TWO-PART REDUCING AGENT/ HUMECTANT SHAVING SYSTEM FOR IMPROVED SHAVING COMFORT

This application is a division of Ser. No. 08/247,915 filed May 23, 1994, now U.S. Pat. No. 5,500,210.

FIELD OF THE INVENTION

This invention relates to a method and composition for improving shaving comfort. More particularly, this invention relates to the sequential application of two compositions which combine to provide superior hair softening which results in reduced cutting forces, whereby a more comfortable shave is achieved.

BACKGROUND OF THE INVENTION

Experience and testing have shown that softening of the hair fiber prior to shaving is of paramount importance to achieving a comfortable shave. Normal applications of water and shaving preparations take three or more minutes to fully hydrate and soften the hair, thereby providing the least resistance to cutting and giving the most comfortable shave. However, the majority of shavers do not choose to wait that length of time and, on average, prepare their hair for one minute or less prior to shaving, leaving considerable room for improvements in comfort.

The major barrier to penetration of water and other materials into the hair is the cuticle, the hair's outermost layers of highly crosslinked keratin protein. It is known that reducing agents which break the sulfur to sulfur or disulfide bonds, that give hair its strength and rigidity, will modify this cuticle layer and increase the rate of water penetration into the hair after treatment. This can be shown through changes in tensile properties of hair, such as stress relaxation, yield stress and rate of water uptake in treated compared to non-treated hairs. It is believed that this breakage of disulfide bonds makes the hair more porous, allowing water to enter more easily and rapidly.

It is now well-known to utilize reducing agents for waving or straightening hair, and as depilating agents for removal of hair without shaving when used at higher concentrations and pH's. See, for example, Balsam and Sagarin, Cosmetics Science and Technology, vol. 2, pages 39–72 and 167–278 (2nd ed. 1972). The use of a reducing agent in a shaving cream or pre-shave lotion has been suggested in U.S. Pat. No. 3,728,356, U.S. Pat. No. 4,775,530 and U.S. Pat. No. 4,935,231 and the possibility of incorporating a depilatory agent in a cartridge razor lubricating strip has been mentioned in U.S. Pat. No. 4,170,821. Compositions containing a depilatory agent and a sodium soap to increase the speed of depilation have been disclosed in U.S. Pat. No. 4,121,904. It is also disclosed in U.S. Pat. No. 4,913,900 and EP 551,135 that moisturizing agents and humectants may be added to hair waving compositions containing reducing agents to reduce damage to the hair and improve softness.

SUMMARY OF THE INVENTION

The present invention comprises a method of improving shaving comfort by softening the hair to be shaved so as to reduce the cutting force required to cut it. The novel method comprises carrying out the following sequential steps:

(a) contacting an area of hair to be shaved with a reducing agent that breaks disulfide linkages in hair;

(b) contacting the area of hair treated in step (a) with a humectant and allowing it to dry or partially dry;

(c) contacting the area treated in step (b) with water to hydrate the hair; and (d) shaving the hydrated hair of step (c).

A preferred way of carrying out the method of the present invention comprises the following sequential steps:

(a) contacting an area of hair to be shaved with a reducing agent that breaks disulfide linkages in hair and water;

(b) shaving the area of hair treated in step (a);

(c) contacting the shaved area of step (b) with a humectant and allowing it to dry or partially dry; and (d) repeating steps (a), (b), and (c) at least once.

In carrying out the above method, the reducing agent is preferably included in a first dermatologically acceptable vehicle and the humectant is preferably included in a second dermatologically acceptable vehicle. The present invention also embraces a novel shaving system comprising in separate containers packaged for use in combination (a) a first dermatologically acceptable vehicle containing a reducing agent which is capable of breaking disulfide linkages in hair; and (b) a second dermatologically acceptable vehicle containing a humectant.

It has been discovered that the afore-described sequential application to the hair of a reducing agent followed by a humectant provides superior and rapid softening of the hair fiber upon rehydration prior to shaving, resulting in easier cutting of the hair, thereby providing a smoother, more comfortable shave. The two-step pretreatment allows hair to hydrate and soften more quickly than untreated hair, hair treated with either agent alone, or hair treated with both agents simultaneously. Moreover, the two-step pretreatment provides for superior softening with reduced irritancy because the reducing agent can be effectively utilized at lower concentrations and less alkaline pH's when followed by the humectant. Thus, the present invention provides a more comfortable shave even with shorter preparation times.

DETAILED DESCRIPTION OF THE INVENTION

Reducing agents which are capable of breaking disulfide bonds in hair keratin are well-known in the field of hair waving, hair straightening and hair depilation. Typical of such materials are the water soluble mercaptans such as thioglycolic acid, thiolactic acid, cysteine, cysteine ethyl ester, cysteine methyl ester, N-acetyl cysteine, cysteamine, thioglycerol, thioglycolic hydrazide, thioglycolamide, glycerol monothioglycolate, β-mercaptopropionic acid, N-hydroxyethyl-mercapto-acetamide, N-methyl-mercapto-acetamide, β-mercapto-ethylamine, β-mercaptopropionamide, 2-mercapto-ethane-sulfonic acid, α-mercaptoethanol, 1,3-dithio-2-propanol, 1,4-dithio-2-butanol, 1,4-dimercapto-2,3-butanediol, 1,3-dithio-2-methoxypropane, 1,3-dimercapto-2-aminopropane, 1,4-dimercapto-2,3-diaminobutane, dimercaptoadipic acid, mercaptopropionic acid, dithiothreitol, homocysteinethiolactone, N-mercaptoalkylgluconamides, N-(mercaptoalkyl) ω-hydroxyalkylamides, thioglyceryl alkyl ethers, 1-phenyl-2-mercaptoethanol and salts of the aforementioned agents where appropriate, such as the ammonium, sodium, potassium, calcium, magnesium or mono- or diethanolamine salts, which are known to be active. Other known reducing agents include ammonium, sodium and potassium sulfites and bisulfites, sodium or potassium borohydride, barium sulfide and metal siliconates of the formula $R_a$—Si—$(O^-M^+)_{4-a}$ as described in U.S. Pat. No. 4,985,240. Of these, the preferred reducing agents include the ammonium, sodium, potassium, calcium, magnesium and mono- or diethanolamine salts of thioglycolic acid, cysteine, cysteamine, cysteine hydrochloride, cysteine methyl ester, cysteine ethyl ester, N-acetyl cysteine, diammonium dithioglycolate, and the ammonium, sodium and potassium sulfites and bisulfites.

The reducing agent, or a mixture of reducing agents, is preferably incorporated in a first dermatologically acceptable vehicle at a concentration which is sufficient to soften the protein structure of the hair without causing depilation or significant skin irritation. The concentration of the reducing agent will typically fall within the range of about 0.2 to 20% by weight depending upon the activity of the particular reducing agent employed. The pH of the vehicle should be adjusted to between 5 and 12.5 to balance optimum activity of the particular reducing agent employed versus skin irritancy, and should preferably fall between 6 and 10. The vehicle will preferably contain a substantial amount of water, most preferably about 60 to 98% by weight.

The vehicle containing the reducing agent may also include a wide variety of other optional components depending upon the form and characteristics of the vehicle which are desired. For example, it may include agents which are known to promote swelling of the hair and/or enhance penetration of the reducing agent such as, for example, urea, thiourea, guanidine, amino guanidine and biguanide. Such agents are typically present at concentrations ranging from about 0.1M to about 2.0M. The vehicle may also optionally include surfactants, fillers, gelling agents, thickeners, emollients, moisturizers, fragrances, coloring agents, and preservatives. However, ingredients which would tend to coat the hair and impede penetration of water and the reducing agent should generally be avoided. Such ingredients are typically hydrophobic and include various types of oils and fatty materials.

It is preferred that the vehicle containing the reducing agent is in the form of a cream, foam, lotion or gel, and most preferably a shaving cream, foam or gel. Such a formulation will typically comprise about 70 to 90% water and about 5 to 25%, preferably about 10 to 20%, of a surface active foaming agent selected from one or more water-soluble soaps, anionic surfactants and non-ionic surfactants. Naturally, of course, the shaving formulation may contain a variety of well-known cosmetic ingredients which are typically used to enhance the performance attributes and aesthetics thereof.

Humectants are hygroscopic agents which are well-known in the cosmetic field. Suitable humectants are those which penetrate the hair and allow it to rehydrate quickly. The most common humectants are the polyhydric alcohols or polyhydroxy alkanes such as, for example, ethylene glycol, glycerin, propylene glycol, dipropylene glycol, triethylene glycol, 1,3-propanediol, butylene glycol, and sorbitol. Other suitable humectants include sodium pyroglutamate, N-acetylethanolamine, sodium lactate, isopropanol, polyalkylene glycols of the formula

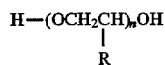

$$H-(OCH_2CH)_n OH$$
$$\phantom{H-(OCH_2}|$$
$$\phantom{H-(OCH_2C}R$$

wherein R is H or $CH_3$ and n has an average value of about 2 to about 10, polyethylene glycol glyceryl ethers, and a variety of other ethoxylated and/or propoxylated chemical agents which are small enough to penetrate hair (e.g. molecular weight of 500 or less) and enhance its ability to rehydrate. Preferred humectants include glycerin, triethylene glycol, 1,3-propanediol, sodium pyroglutamate, sodium lactate, N-acetyl-ethanolamine and sorbitol.

The humectant, or a mixture of humectants, is preferably incorporated in a second dermatologically acceptable vehicle, generally at a concentration of about 5 to 50% by weight, preferably about 10–30%. The vehicle will preferably contain a substantial amount of water, generally from about 40 to about 90% by weight. The pH of the vehicle may be adjusted to suit the particular characteristics which are desired, but will preferably be approximately neutral (e.g. pH 5–8). The vehicle may contain a wide variety of other cosmetic ingredients depending upon the form and and characteristics of the vehicle which are desired. However, hydrophobic substances which might interfere with penetration of water and humectant into the hair should be avoided. The vehicle may include low to moderate amounts of alcohol as well as one or more agents known to swell hair.

It is preferred that the vehicle containing the humectant is in the form of an aftershave splash, lotion or gel. Such formulations will typically comprise about 20 to 80% water, about 0 to 50% ethyl alcohol, about 5–50% humectant, fragrance and optional thickening agent.

In a preferred method of practicing the present invention the first step will involve contacting the area of hair to be shaved with an aqueous shaving preparation, such as a conventional shaving cream or gel, which shaving preparation also contains a reducing agent. The area is then shaved and rinsed. The shaved area is then contacted with an aftershave preparation, such as an aftershave splash or gel, which contains a humectant which penetrates the shaved hair, allowing it to later rehydrate more quickly. When the hair in the shaved area has regrown and is ready to be shaved again, presumably the next day, it is hydrated by contacting it with water and preferably with the same or similar reducing-agent-containing shave preparation used in the first step. It may then be shaved again, rinsed, and the process repeated as many times as desired.

Since the advantage of the present invention is fully realized after both the reducing agent and humectant have been applied, it should be obvious that the second and subsequent shaves following the afore-described regimen will give the maximum benefit of increased smoothness and comfort over conventional shaving regimens. Naturally, since there are many possible ways of carrying out the two-step pretreatment of the present invention, the invention is not limited to the aforedescribed technique which merely represents one of the more practical embodiments thereof.

The invention may be further illustrated by reference to the following example:

EXAMPLE 1

Facial beard hair was collected from men with 2 to 3 inches of beard growth which had not been treated with colorants, oxidizing or reducing agents or oily conditioners or regularly exposed to chemical fumes (e.g. professional painters) or sun. Hairs to be utilized in tests were preselected for pigmentation, 3 mil minor diameter (major diameter averaged 6 to 6.5 mils) and the presence of a consistent medulla in the fiber. Most tests utilized cheek fibers, but chin fibers may be used.

A small segment of beard hair was divided in half, with one half being treated as the test element and the other half as the control element. The test elements were immersed in a test material (aqueous reducing agent) for a set period of time (e.g. 3 min.) as indicated, and the control elements were likewise immersed in a control material (e.g. Foamy shave cream). They were then removed, rinsed in running tap water for about 30 seconds and then immersed in the test material (humectant) or control material (e.g. water) for a set period of time (e.g. 3 min.). After removal, the hairs were allowed to air dry and equilibrate for a minimum of 18 hours at 70° F.±1° and 65%±2% relative humidity in a constant temperature and humidity room.

Cuts were made on a Free End Cutting Force Instrument, which utilizes a linear variable differential transformer configured as a load cell (similar to that used in a weighing balance) to detect the peak amount of force in grams required for a razor blade to cut through a beard hair. The hairs were cut in a free-end mount, that is the part of the hair to be cut is unsupported, and the blade cuts through the minor diameter, with the major diameter parallel to the blade edge. Test and control hairs were taped to small metal anvils for cutting and oriented such that cuts on the paired segments occur within a 1 mm distance on the original intact segment (i.e. before being divided into paired segments). Cuts made in this manner significantly reduced the effects of the normal high variability along the length of a beard fiber. Anvil mounted hairs were immersed in water or other hydrating material by inverting the anvil and supporting it over the container in such a way that all of the exposed hair and only a very small corner of the anvil was immersed. After about 55 seconds immersion, the anvil was immediately placed in the anvil holder on the cutting force instrument and the hair cut. The entire hydrating-cutting process was completed within about 65 seconds.

Data was calculated as the average of ratios of treated over control peak cutting forces for each pair of hairs. Ten to fourteen pairs were cut per test. The percent change (decrease or increase) in cutting force was calculated from the average of the ratios. The results of several tests are presented in the Table.

TABLE

| Treatment | Control | Decrease In Cutting Force |
|---|---|---|
| A (1) 11.5% Cysteine pH 9.5 - 4 min. | Foamy Reg. | 14.5% |
| (2) 25% aq. glycerin - 3 min. | Water | |
| B (1) 11.5% Cysteine pH 10.0 - 4 min. | Foamy Reg. | 23.5% |
| (2) 25% aq. glycerin - 3 min. | Water | |
| C (1) 15.5% Cysteine pH 10.0 - 4 min. | Foamy Reg. | 20.7% |
| (2) 25% aq. glycerin - 3 min. | Water | |
| D (1) 8.2% N-Acetyl Cysteine pH 10.0 - 4 min. | Foamy Reg. | 11.2% |
| (2) 25% aq. glycerin - 3 min. | Water | |
| E (1) 4.0% Ca Thioglycolate pH 9.5 - 4 min. | Foamy Reg. | 15.4% |
| (2) 25% aq. glycerin - 3 min. | Water | |
| F (1) 3.3% $NH_3$ Thioglycolate pH 9.5 - 10 min. (no water rinse) | 3.3% $NH_3$ Thioglycolate | 28.6% |
| (2) 25% aq. glycerin - 10 min. | Water | |
| G (1) 15% Cysteine HCl pH 9.5 - 4 min. | Foamy Reg. | 11.0% |
| (2) 25% aq. triethylene glycol - 3 min. | Water | |
| H (1) 16.2% Cysteine methyl ester HCl pH 9.5 - 4 min. | Foamy Reg. | 21.0% |
| (2) 25% aq. glycerin - 3 min. | Water | |
| I (1) 1.7% Cysteamine-HCl pH 9.5 - 3 min. | Foamy Reg. | 10.2% |
| (2) 25% aq. glycerin - 3 min. | Water | |
| J (1) Foamy Reg. - 10 min. | Foamy Reg. | none |
| (2) 25% aq. glycerin - 10 min. | Water | |

Example A was repeated but with the following humectants substituted for glycerin: triethylene glycol, 1-3-propanediol, pyroglutamic acid sodium salt, N-acetylethanolamine, sodium lactate, sorbitol and ethylene glycol. The decrease in cutting force compared to the control ranged from 7 to 15%.

EXAMPLE 2

Panels of 8 to 10 men applied an aqueous solution of reducing agent to one side of their faces and water to the other side of their faces as a control. Both the reducing agent solution and the water were thickened to a thin gel with a water soluble hydroxyethylcellulose gum to permit the materials to remain on the face and to prevent them from drying out during the treatment time. One minute after application, panelists made three strokes with a twin blade razor in the central cheek area on each side of their faces and rated the sensation of pull on each side on a 10 point scale (0=no pull, 10=excessive pull). The test and control materials were then left on the face for an additional 2 to 3 minutes for a total treatment time of 3 to 4 minutes. The panelists then rinsed the materials off, applied a shave foam and completed shaving the rest of the face. After rinsing and drying the face, the same amount of aqueous humectant aftershave (25% glycerin) was applied to both sides of the face and remained on the face until the panelist washed his face later in the day. Panelists followed this procedure Monday through Friday of the first week of the study, used their regular shaving routine Saturday and Sunday, and continued with the same test procedure outlined for the first week during the second week, but with the sides of the face on which the reducing agent and water solutions were applied being switched. Panelists were not informed which sides of their face received the test and control materials. Using this test procedure, panelists have rated, on average, that the side of the face receiving the reducing agent/ humectant application resulted in decreased pull compared to the control. The reducing agent solutions tested in this manner included cysteine (11.5%), N-acetyl cysteine (15.5%), Cysteamine HCl (1.0%) and $NH_3$ thioglycolate (3.3%).

What is claimed is:

1. A shaving system consisting essentially of, in separate containers packaged for use in combination,
    (a) a shaving cream, foam or gel comprising about 70 to 90% water, about 5 to 25% of a surface active foaming agent selected from one or more water-soluble soaps, anionic surfactants and non-ionic surfactants, and about 0.2 to 20% of a reducing agent that breaks disulfide linkages in hair; and
    (b) an aftershave splash, lotion or gel comprising about 20 to 80% water, about 0 to 50% ethyl alcohol, and about 5 to 50% of a humectant.

2. The shaving system of claim 1 wherein the reducing agent is selected from the group consisting of thioglycolic acid, thiolactic acid, cysteine, cysteine ethyl ester, cysteine methyl ester, N-acetyl cysteine, cysteamine, thioglycerol, thioglycolic hydrazide, thioglycolamide, glycerol monothioglycolate, β-mercaptopropionic acid, N-hydroxyethyl-mercapto-acetamide, N-methyl-mercapto-acetamide, β-mercaptoethylamine, β-mercaptopropionamide, 2-mercapto-ethane-sulfonic acid, α-mercaptoethanol, 1,3-dithio-2-propanol, 1,4-dithio-2-butanol, 1,4-dimercapto-2,3-butanediol, 1,3-dithio-2-methoxypropane, 1,3-dimercapto-2-aminopropane, 1,4-dimercapto-2,3-diaminobutane, dimercaptoadipic acid, mercaptopropionic acid, dithiothreitol, homocysteinethiolactone, N-mercaptoalkylgluconamides, N-(mercaptoalkyl) ω-hydroxyalkylamides, thioglyceryl alkyl ethers, 1-phenyl-2-mercaptoethanol, the ammonium, sodium, potassium, calcium, magnesium or mono- or diethanolamine salts of the aforementioned agents, the ammonium, sodium and potassium sulfites and bisulfites, sodium or potassium borohydride, barium sulfide and metal siliconates of the formula $R_a\text{—Si—}(O^-M^+)_{4-a}$.

3. The shaving system of claim 2 wherein the humectant is selected from the group consisting of ethylene glycol, glycerine, propylene glycol, dipropylene glycol, triethylene glycol, 1,3-propanediol, butylene glycol, sorbitol, sodium pyroglutamate, N-acetylethanolamine, sodium lactate, isopropanol, polyalkylene glycols of the formula

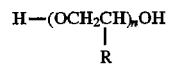

wherein R is H or $CH_3$ and n has an average value of about 2 to about 10, and polyethylene glycol glyceryl ethers.

4. The shaving system of claim 1 wherein the reducing agent comprises cysteamine.

5. The shaving system of claim 1 wherein the humectant comprises glycerine.

* * * * *

UNITED STATES PATENT AND TRADEMARK OFFICE
CERTIFICATE OF CORRECTION

PATENT NO. : 5,665,340
DATED : Sep. 9, 1997
INVENTOR(S) : Stoner et al.

It is certified that error appears in the above-indentified patent and that said Letters Patent is hereby corrected as shown below:

On the cover page, under Section [56] References Cited, please insert the following additional references.

U.S. PATENT DOCUMENTS

| | | | |
|---|---|---|---|
| 4,935,231 | 6/1990 | Pigiet | 424/71 |
| 4,775,530 | 10/1988 | Perricone | 424/73 |
| 3,728,356 | 4/1973 | Yablonsky | 260/309 |
| 4,170,821 | 10/1979 | Booth | 30/41 |
| 4,121,904 | 10/1978 | Schamper | 8/161 |
| 4,913,900 | 4/1990 | Kolc et al | 424/72 |
| 3,981,681 | 9/1976 | De La Guardia | 8/161 |
| 4,618,344 | 10/1986 | Wells | 8/161 |
| 4,631,064 | 12/1986 | Juneja | 8/161 |
| 5,387,412 | 2/1995 | Moore | 424/73 |
| 4,944,939 | 7/1990 | Moore | 424/73 |
| 3,708,431 | 1/1973 | Prussin | 424/73 |
| 5,456,907 | 10/1995 | Nandagiri | 424/70.51 |
| 5,225,191 | 7/1993 | de Labbey | 424/71 |

FOREIGN PATENT DOCUMENTS

| | | |
|---|---|---|
| 551,135 | 7/1993 | European Pat. Off. |

OTHER PUBLICATIONS

Remington's Pharmaceutical Sciences, 18th Ed., p.762 (1990)

Signed and Sealed this

Twenty-fifth Day of November, 1997

*Attest:*

BRUCE LEHMAN

*Attesting Officer*  *Commissioner of Patents and Trademarks*